United States Patent [19]

Honour et al.

[11] Patent Number: 5,529,923
[45] Date of Patent: Jun. 25, 1996

[54] FLAVOBACTERIUM STRAIN

[75] Inventors: Richard C. Honour, Seattle; John J. Majnarich, Mercer Island, both of Wash.

[73] Assignee: Isomeric Corporation, Redmond, Wash.

[21] Appl. No.: 194,662

[22] Filed: Feb. 14, 1994

[51] Int. Cl.$^6$ ..................................................... C12N 1/20
[52] U.S. Cl. ..................................... 435/252.1; 435/850
[58] Field of Search ................................ 435/252.2, 850, 435/252.1

[56] References Cited

U.S. PATENT DOCUMENTS

| | | | |
|---|---|---|---|
| 3,879,260 | 4/1975 | Kanamitsu | 195/28 |
| 4,885,171 | 12/1989 | Surendra et al. | 424/122 |
| 5,066,493 | 11/1991 | Sehgal et al. | 424/122 |

FOREIGN PATENT DOCUMENTS 45-37079  11/1970  Japan .

OTHER PUBLICATIONS

Oyaizu, et al., "Chemotaxonomic and Phenotypic Characterization of the Strains of Species in the Flavobacterium–Cytophaga Complex," *J. Gen. Appl. Microbiol*, 27, 57–107 (1981).

Umezawa, et al., "Marinactan, Antitumor Polysaccharide Produced by Marine Bacteria," *The Journal of Antibiotics*, vol. XXXVI, No. 5, 471–477 (May 1983).

*Primary Examiner*—Irene Marx
*Attorney, Agent, or Firm*—Townsend and Townsend and Crew

[57] ABSTRACT

The present invention includes a substantially pure bacterium, *Flavobacterium spp.*, which produces compositions having unique anti-tumor and anti-inflammatory properties. The present invention includes methods for treating tumors in mammals comprising administering to such mammals a therapeutically effective amount of a composition of the invention.

2 Claims, 7 Drawing Sheets

FLAVOBACTERIUM STRAIN

BACKGROUND OF THE INVENTION

Mankind is constantly searching for new drugs to cure its afflictions. Of all of mankind's ills none has engendered a greater effort to find new drugs than cancer. The long, and largely fruitless, search for new and more effective treatments for cancer has led many scientists to reconsider the long-held belief that chemists could derive effective anti-tumor compositions merely by trial and error in the laboratory. These scientists have realized that nature provides a far greater variety of medicinal compounds synthesized by plants than could ever be made at the laboratory bench. Thus, attention has turned to the jungles and forests of the world as a storehouse of new and effective anti-tumor compounds. For example, the drug Taxol, found in the Pacific Yew, has a structure few medicinal chemists would have derived a priori. Yet, this compound has shown strong anti-tumor properties.

Several important anti-tumor compounds have been isolated from microorganisms. For example, bleomycin $A_2$ and $B_2$ are produced by *Streptomyces verticulls*. These compounds are used in the treatment of testicular cancer, squamous cell carcinoma, and Hodgkin's disease. Dactinomycin, isolated from *Streptomyces antibioticus*, has been used successfully against choriocarcinoma, Wilms tumor and testicular tumors. Cyclosporine, a metabolite of *Cylindrocarpon lucidum* and *Trichoderma polysporum* is an immunosuppressive and is effective against severe aplastic anemia. Thus, microbes continue to be a source of effective anticancer compounds.

SUMMARY OF THE INVENTION

The present invention includes a substantially pure culture of a unique microorganism, *Flavobacterium spp.*, ATCC Number 55435, which produces unique compositions effective for treating tumors.

In another aspect, the present invention includes a unique composition, MRR-21, which is produced by the *Flavobacterium spp.* bacterium. This composition has shown biological activity in vitro and in vivo as an anti-tumor agent when tested against a number of human and murine cancer cell lines, including leukemias, melanomas, and colon and renal cancer cell lines. Thus, the present invention further includes a method of treating tumors in a mammal, comprising administering to said mammal a therapeutically effective amount of MRR-21.

More specifically, the present invention includes a method of treating leukemia in a mammal, comprising administering to said mammal a therapeutically effective amount of MRR-21. The present invention also includes a method of treating renal cancer in a mammal, comprising administering to said mammal a therapeutically effective amount of MRR-21; a method of treating colon cancer in a mammal, comprising administering to said mammal a therapeutically effective amount of MRR-21; and a method of treating melanoma in a mammal, comprising administering to the mammal a therapeutically effective amount of MRR-21.

In yet another aspect, MRR-21 has useful anti-inflammatory properties. Thus, the present invention also includes a method of treating inflammation in a mammal, comprising the administration of a therapeutically effective amount of MRR-21 to a mammal having an inflammatory condition.

These and other aspects of the invention will be become more apparent when the following Description is read with the accompanying Drawings.

DESCRIPTION OF SPECIFIC EMBODIMENTS

Figure 1A:
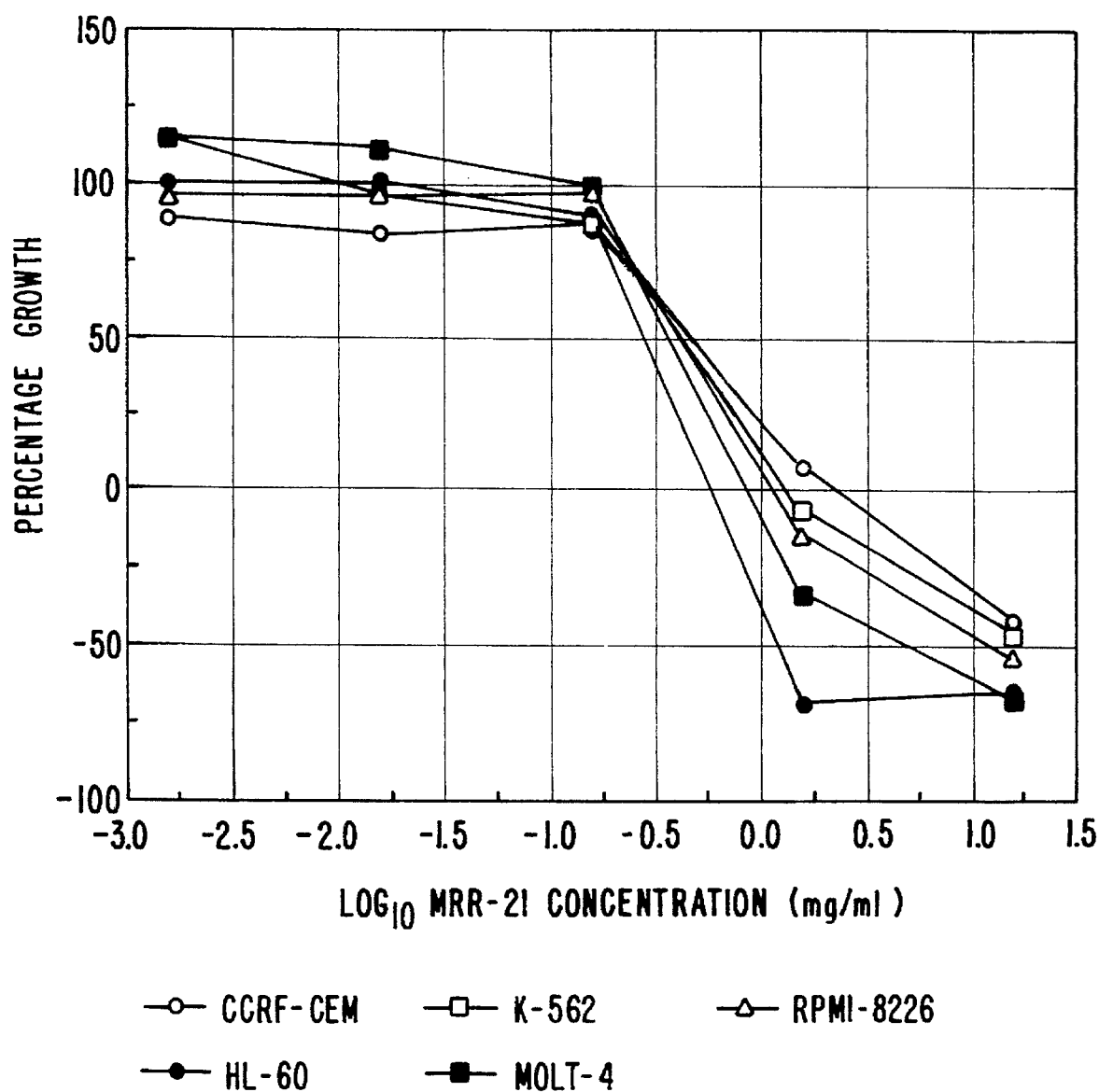
FIGS. 1A–D show dose response curves which demonstrate the activity of MRR-21 against various leukemia, melanoma, and renal and colon cancer cell lines, respectively.

The present invention includes a substantially pure culture of *Flavobacterium spp.* cells, ATCC Accession Number 55435, and methods of preparing such a culture. "Substantially pure" refers herein to bacterial or chemical material which is substantially or essentially free from components that normally accompany the material in its native state. A composition is substantially pure if it does not contain materials normally associated with their in situ environment, e.g., bacterial proteins. A substantially pure bacterial material is one essentially free of bacterial species which do not produce the compound of the invention.

The bacteria of the present invention belong to the genus Flavobacterium. The genus Flavobacterium includes gram-negative, nonsporeforming, rod-shaped cells which do not show motility in a hanging drop. These bacteria are aerobic, and oxidize, but not ferment, maltose and other carbohydrates. Most species produce indole and some may produce a water-insoluble yellow pigment. Flavobacteria are widely distributed in soil and water, and are commonly found on vegetables, meats, dairy products, poultry and in hospital environments. See, McGraw-Hill, ENCYCLOPEDIA OF SCIENCE AND TECHNOLOGY, Vol. 7, p. 136 (McGraw-Hill 1987).

The classification of the strain of the present invention may be carried out according to the methods disclosed in BERGEY'S MANUAL OF SYSTEMATIC BACTERIOLOGY, Vol. 1, 1984, which is incorporated herein by reference. Cells of the bacterium of the invention vary from coccobacilli to tiny slender rods, depending on the growth medium used. In a preferred growth medium described below, the cells appear as rods having dimensions 0.5–0.7 by 1.0–3.0 microns. The cells are motile and have a swarming movement. They are gram negative and do not form endospores. Growth on solid media is pigmented from yellow to orange, with the most pronounced pigment (reddish-orange) being formed on potato-starch media. The temperature range for pigmentation and growth are from 27°–30° C., with the optimal temperature range for pigmentation from 26°–28° C. However, early colonies may appear opaque and are not pigmented. During fermentation in carbohydrate media (e.g., sucrose or starch) there is a slight change in pH to the acidic. The bacterial strain of the present invention further includes the following characteristics.

TABLE 1

| Carbohydrate Utilization: | |
|---|---|
| D-arabinose | − |
| L-arabinose | + |
| D(+)cellobiose | + |
| D-glucose | + |
| D-galactose | + |
| β-Lactose | + |
| D-lereulose | + |
| D(+)mannose | + − |
| Raffinose | − |
| D-Ribose | + − |
| L-Sorbose | − |
| Trehalose | + |
| D-Xylose | − |
| Glyceral | − |
| Salicin | − |
| Soluble Starch | + |
| Dulcitol | − |
| D-Mannitol | + |
| D-Sorbitol | − |
| Hydrolysis of: | |
| gelatin | + |
| casein | + |
| starch | + |
| agar | − |
| cellulose | − |
| chitin | − |
| Acid from: | |
| glucose | − |
| lactose | + − |
| sucrose | + |
| maltose | + |
| amygdalin | + |
| arabinose | + |
| mannose | + |
| Hydrolysis of ONPG: (Orthonitrophenol) | + |
| Hydrolysis of arginine: dihydrolase | + |
| Methyl red | − |
| Citrate | − |
| Indole | − |
| Hydrogen sulfide | − |
| Nitrate to nitrite | + |
| Catalase | + |

The cell culture of the invention may be prepared by techniques which are well-known. Generally, the isolated *Flavobacterium spp.* cells are placed on a nutrient medium which is effective to support growth of the bacterial population. Such media include nutrient complexes such as yeast extract, a nitrogen source, one or more carbon sources and a calcium source. The medium may include a solid support, such as a solid agar support. The bacterium is incubated in the medium under substantially aerobic conditions, using standard methods and implements, as described in BIOTECHNOLOGY APPLICATIONS AND RESEARCH, Cheremisinoff, et al., Eds. (Technomic Publishing Co., Lancaster, Pa.) 1985; and Biotechnol. Prog. 7; 246–250 1991, both of which are incorporated herein by reference).

When the culture population has achieved sufficient density, as indicated by the formation of at least one substantially discrete bacterial colony, a portion of the colony is removed using known techniques (e.g., a bacteriological transfer needle). This aliquot is grown in a liquid culture broth having the same ingredients, and in the same concentrations, as the solid support medium described above, but without the agar. Upon reaching a sufficient density, a second aliquot is taken from the culture and grown until log-phase growth of the colony is achieved. Once the culture has achieved sufficient density, the cells are isolated using standard techniques such as centrifugation or filtration.

In one preferred embodiment, the isolated *Flavobacterium spp.* cells are placed on a solid starch agar support (available from Difco) which contains a nutrient medium including NZ Amine Type A (Sheffield Chemical Co., Norwich, N.Y.), Yeast Extract (Difco), soluble starch (Difco), dextrose, and calcium carbonate (both from Sigma, St. Louis, Mo.). The NZ Amine Type A comprises between about 0.1% and 2.0% of the medium, more preferably between about 0.1% and 1.0%, and most preferably about 0.5% by weight. The Yeast Extract (Difco) comprises between about 0.1% and 2.0% of the medium, preferably between about 0.1 and 1.0% and more preferably about 0.5% by weight. The soluble starch comprises between about 0.1 and 2.0% of the medium, preferably between about 0.1 and 1.0%, and more preferably 0.5% by weight. The dextrose component comprises between about 0.1% and 2.0% of the medium, more preferably between about 0.1% and 1.0% and most preferably 0.5% by weight; the calcium carbonate component comprises between about 0.1% and 2.0% of the medium, more preferably between about 0.1% and 1.0% and most preferably 0.5% by weight.

The cells are incubated on this medium, under substantially aerobic conditions, for a period sufficient to form a discrete bacterial colony on the medium surface. This period is preferably between about 4 and 9 days, more preferably between about 5 and 8 days, and most preferably about 7 days. An aliquot from the surface of the medium is taken using a standard bacteriological transfer needle and is used as inoculum to start a liquid culture broth. In one preferred embodiment, the broth comprises the same ingredients just described for the nutrient medium, except the starch is excluded. Typically, a bacterial sample from a discrete colony is placed in 250 ml of the liquid broth and is maintained at about ambient temperature, preferably for between about 15 and 30 hours, more preferably between about 20 and 28 hours, and most preferably about 24 hours.

When the cells have reached log-phase growth, which is defined to be the period of growth during which the logarithm of the cell mass increases linearly with time (see, MICROBIOLOGY 3rd ed., Davis, et al., Eds., which is incorporated herein by reference) a small amount of bacteria-containing material is withdrawn from the liquid broth and placed in a container, such as a fermenter. In one preferred embodiment, about 150 ml of the liquid broth is added to 15 L of the above-described liquid broth which is contained in a 20 L fermenter, such as a New Brunswick fermenter (Model MF-214/96325). This material is then aerated, preferably for between about 20 and 26 hours, and more preferably for about 24 hours at an aeration rate of between about 40 and 60 ml/min, most preferably about 50 ml/min, of air. The mixture is preferably agitated during this process for a period of between 90 and 100 hours, more preferably for about 96 hours. The means, duration and rates of agitation are determined using well-known methods.

After the cell mass in the larger container has reached log-phase growth, the cells are collected by standard means, such as centrifugation. It will be appreciated that the frequency and duration of the centrifuging will depend on the amount of material in the broth and will be apparent to those of skill. In the example described above, the cells are centrifuged at about 3,000 rpm for about 15 min. This yields a wet cell mass of about 100 g.

The cells are then lysed using standard techniques. Preferably the lysing is performed by combining the cell mass with an EDTA solution comprising about 0.1% and 1.0%, more preferably between about 0.1% and 0.5%, and most preferably about 0.5% EDTA in water. However, other methods of lysing the cells known in the art may be employed, including such methods as sonication or physical or chemical disruption. The lysate is then extracted with one or more lipophilic solvents to remove the lipophilic component from the cells. Preferred solvents include hydrocarbon solvents, and more preferred solvents comprise straight chain alkyls. A most preferred solvent is hexane ($C_6H_{14}$).

The extract is then extracted a second time with an extraction medium comprising a solvent or combination of solvents effective to substantially solvate the desired composition produced by the cell, MRR-21. In one preferred embodiment the extraction medium includes about 10 to 50% chloroform ($CHCl_3$) and between about 10 and 50% ethyl acetate ($CH_3CO_2C_2H_5$). A more preferred medium contains about 15 to 35% chloroform and between about 15 and 35% ethyl acetate, and a most preferred medium contains about 20 to 25% chloroform and between about 20 and 25% ethyl acetate. Other solvent combinations will be apparent to those of skill in the art. The extract is concentrated by standard procedures, for example, using a rotary evaporator, to form a concentrate. The concentrate is washed with a solution effective to remove any remaining hydrophilic species. A preferred solution is 1N sodium carbonate, but any solution of comparable ionic strength will suffice.

The MRR-21 is isolated by standard techniques such as crystallization. In one preferred embodiment, the remaining chloroform/ethyl acetate solution is diluted with an equal volume of water and stored at about 0° C. until a precipitate forms. Other methods of inducing precipitation known in the art may be used as well (see, e.g., Furniss, et al., VOGEL'S TEXTBOOK OF PRACTICAL ORGANIC CHEMISTRY 5th ed. (Longman 1989), which is incorporated herein by reference). The resulting MRR-21 crystals are then isolated by standard techniques, such as filtration through a Büchner funnel, and dried. Generally, 100 grams of wet cell mass yields about 1-2 grams of MRR-21.

Figure 2:
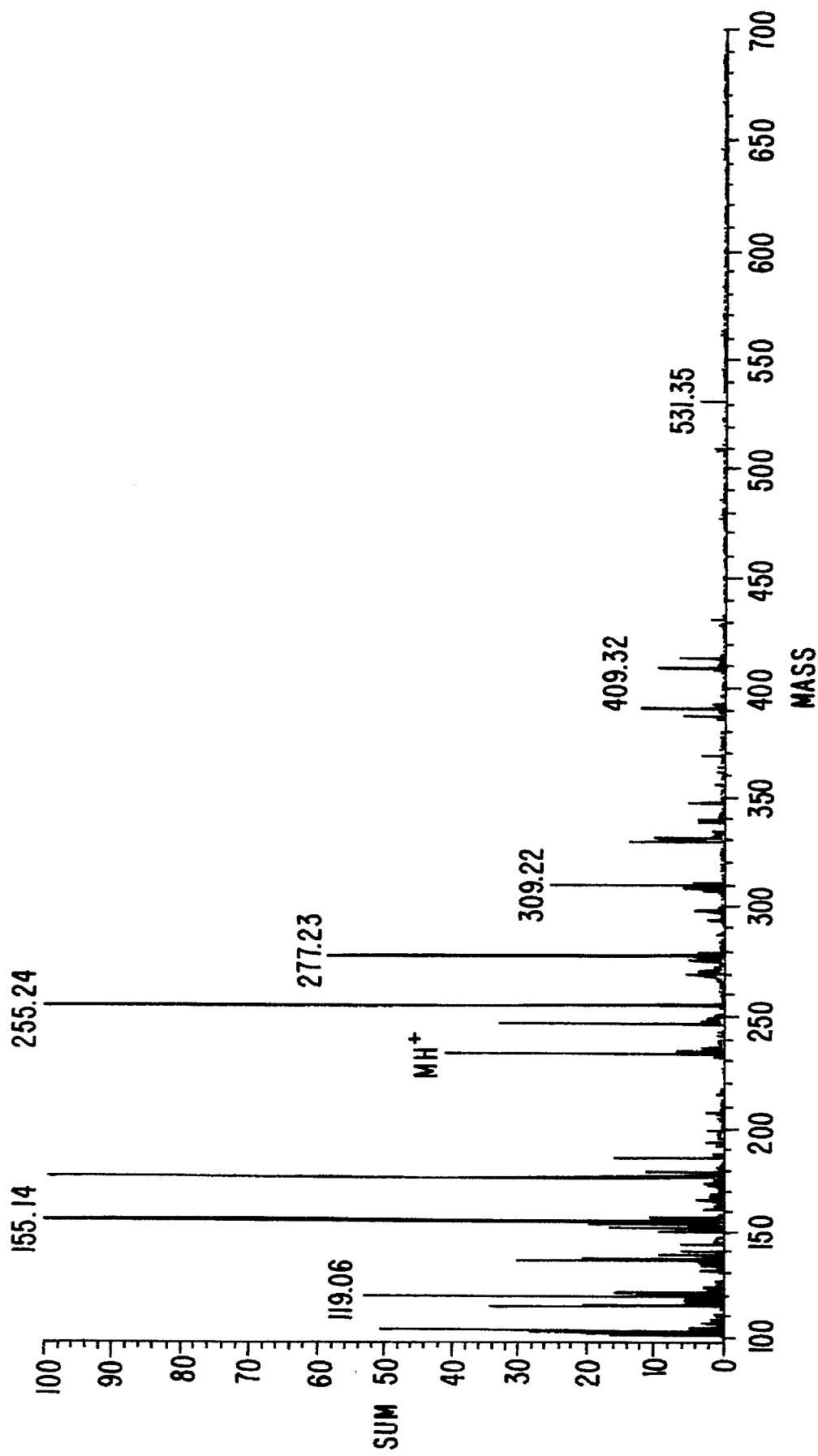
FIG. 2 is a mass spectrograph of crude MRR-21.
Figure 3A:
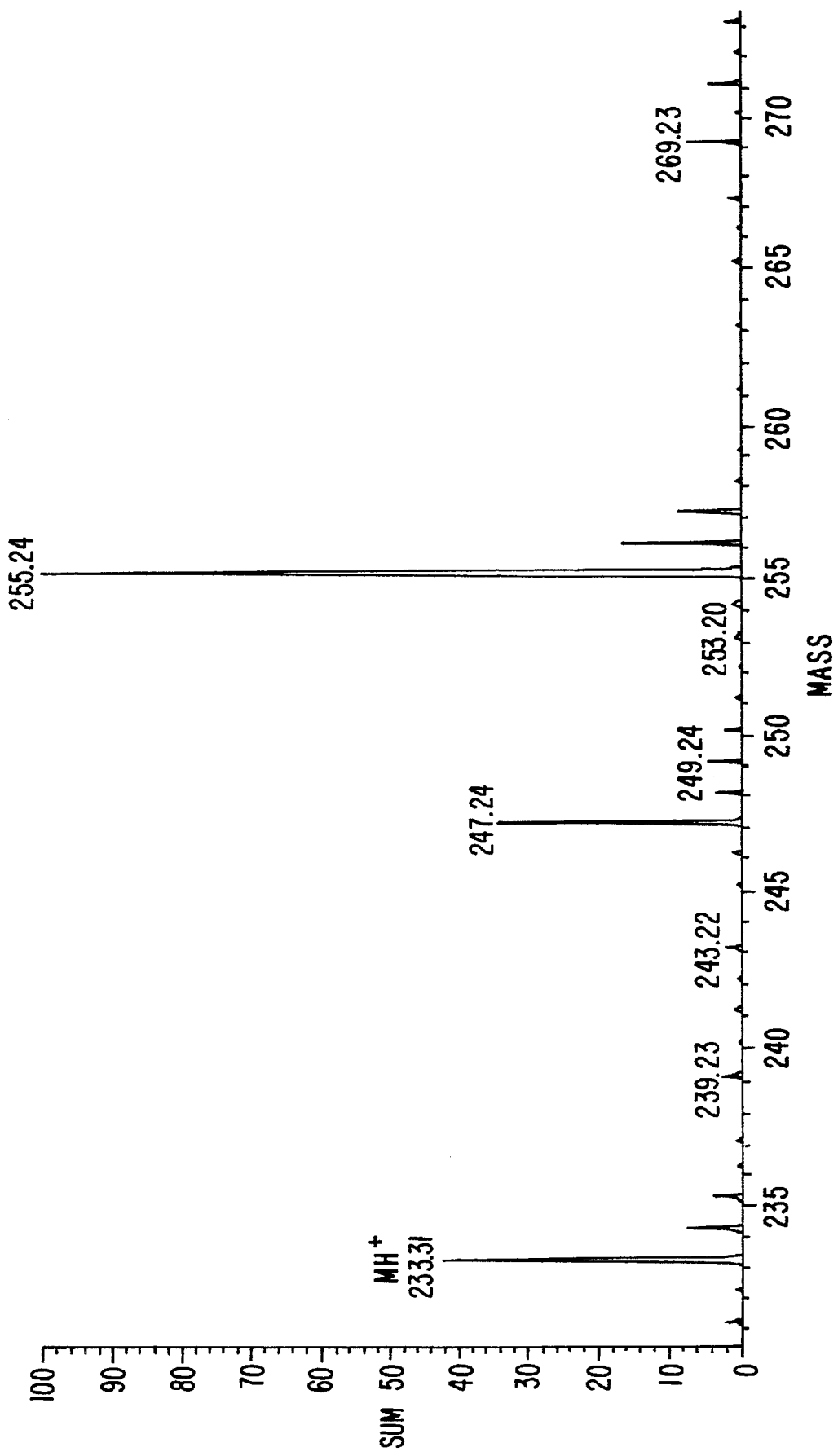
FIG. 3A is a detail of FIG. 2 in the region of the major component of MRR-21.
Figure 3B:
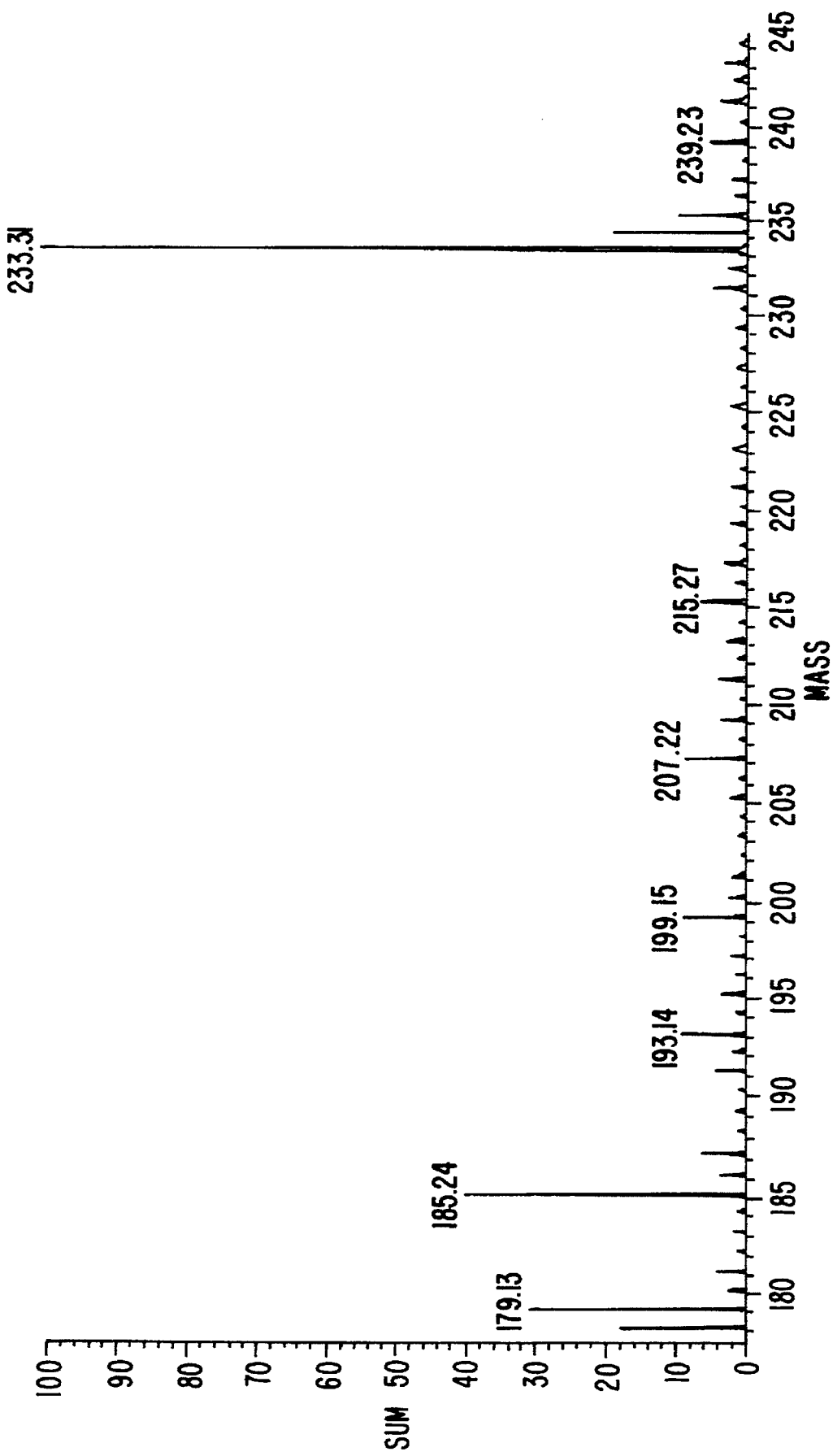
FIG. 3B is a detail of FIG. 2 in the region of the minor component of MRR-21.

The MRR-21 isolated from the *Flavobacterium spp.* may be subjected to further purification to isolate two pure constituent compounds using techniques commonly used in the chemical arts for the isolation of natural products. The mass spectrograph of crude MRR-21 is shown in FIG. 2. This data show a major component having a molecular weight of about 255.24 g/mole and a minor component having a molecular weight of about 233.31 g/mole. Details of the spectrograph shown in FIG. 2 are provided in FIGS. 3A and 3B which focus on the regions of FIG. 2 relating to the major and minor components, respectively.

MRR-21 has been shown to have significant antitumor properties against a number of cancer cell lines including cell lines associated with leukemia, melanoma, renal and colon cancer and Sarcoma-180. The activity of MRR-21 against leukemia, melanoma, renal and colon cancers has been demonstrated by the National Cancer Institute's screening procedures. Generally the screen comprises exposing about 60 cell lines associated with various cancers to several concentrations of the compound in question. The sixty cell lines span nine forms of cancer, including leukemia, non-small cell lung cancer, CNS cancer, ovarian cancer, prostate cancer, breast cancer, colon cancer, renal cancer and melanoma. A standard 48-hour continuous drug exposure protocol is followed. A sulfurhodamine B (SRB) protein assay is employed to determine the viability of cell growth. Parameters which are observed during the screening program include mean response, differential cellular sensitivity, and subpanel-specific patterns of sensitivity. The growth of the cells over time is measured and the percentage growth of the cells over time is determined to yield a dose-response curve.

The activity of MRR-21 was also measured against Sarcoma-180 tumors which had been induced into the hind legs of Swiss Webster mice by injection with Sarcoma-180 cells. Three such trials were performed wherein MRR-21 was administered for 7 days (1) immediately following induction of the tumors, (2) 7 days after tumor initiation, and (3) 14 days after initiation. In the third trial, the mice were observed for an additional 7 days. The mice were sacrificed at the end of each period and their hind legs and tumors weighed. As the data in Example 2 indicate, MRR-21-treated mice showed significant reductions in tumor size as compared to untreated mice.

MRR-21 has also shown inhibitory effects in mice exposed to leukemia P388. In tests to determine the mean survival time of mice exposed to leukemia, mice treated with MRR-21 survived far longer than mice who did not receive treatment with MRR-21. MRR-21 has also exhibited anti-inflammatory activity, as an antiphlogistic. Mice subjected to the granuloma pouch assay were found to exhibit a greatly reduced inflammatory response than mice which were not treated.

In yet another aspect of the invention, it will be appreciated that the *Flavobacterium spp.* bacterium can used as a foodstuff, e.g., in foods such as yoghurt. Such a mode of delivery provides an effect means of delivering MRR-21 through the digestive tract. As MRR-21 has shown effectiveness in treating cancers associated with the digestive tract, such as colon cancer, and has exhibited anti-inflammatory properties, ingestion of the *Flavobacterium spp.* bacterium, e.g., through a capsules, tablets, or in the powdered form of the dried or lyophilized cells, may be well suited for the treatment of conditions associated with the alimentary canal. Techniques for encapsulation, tablet formation, and lyophilization are well-known in the art.

DELIVERY OF MRR-21

As described above, MRR-21 has shown broad antitumor activity. Thus, in another aspect, the present invention includes methods for treating tumors in a mammal, comprising administering to such a mammal a therapeutically effective amount of MRR-21. More specifically, the present invention includes methods for treating leukemia, colon cancer, renal cancer, melanoma and inflammation in a mammal so afflicted, comprising administering to such mammal a therapeutically effective amount of MRR-21.

The compositions containing the compounds described above can be administered for prophylactic and/or therapeutic treatments. In therapeutic applications, compositions are administered to a patient already suffering from a condition, as described above, in an amount sufficient to cure or at least partially arrest the symptoms of the condition and its complications. An amount adequate to accomplish this is defined as "therapeutically effective amount or dose." Amounts effective for this use will depend on the severity and course of the disease, previous therapy, the patient's health status and response to the drugs, and the judgment of the treating physician.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose will be in the range of 0.1 to 1000 milligrams (rag) per recipient per day, preferably in the range of 1 to 100 mg per day. The desired dosage is preferably presented in one, two, three, four or more sub-doses administered at appropriate intervals throughout the day. These subdoses can be administered as unit dosage forms, for example, containing 5 to 1000 mg, preferably 10 to 100 mg of active ingredient per unit dosage form.

The composition used in these therapies can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application.

While it is possible to administer the active ingredient of this invention alone, it is preferable to present it as part of a pharmaceutical formulation. The formulations of the present invention comprise at least one compound of this invention in a therapeutically or pharmaceutically effective dose together with one or more pharmaceutically or therapeutically acceptable excipients or other ingredients. Various considerations are described, e.g., in Gilman, et al. (eds) (1990) GOODMAN AND GILMAN'S: THE PHARMACOLOGICAL BASES OF THERAPEUTICS, 8th Ed., Pergamon Press; and REMINGTON'S PHARMACEUTICAL SCIENCES. Methods for administration are discussed therein, e.g., for oral, intravenous, intraperitoneal, or intramuscular administration, and others. Pharmaceutically acceptable carders will include water, saline, buffers, and other compounds described, e.g., in the *Merck Index,* Merck & Co., Rahway, N.J.

Also included within the invention are preparations for topical application to the skin comprising a compound of the invention, typically in concentrations in the range of from about 0.001% to 10%, together with a non-toxic, pharmaceutically acceptable topical carder. These topical preparations can be prepared by combining an active ingredient according to this invention with conventional pharmaceutical diluents and carders commonly used in topical dry, liquid, cream, gel and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like.

Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

The topical pharmaceutical compositions according to this invention may also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly bacteriostats, antibiotics, anesthetics, analgesics, and antipruritic agents.

The pharmaceutical compositions can be administered by parenteral or oral administration for prophylactic and/or therapeutic treatment. The pharmaceutical compositions can be administered in a variety of unit dosage forms depending upon the method of administration. For example, unit dosage forms suitable for oral administration include powder, tablets, pills, capsules and dragees.

The pharmaceutical compositions can be administered intravenously. Thus, this invention provides compositions for intravenous administration which comprise a solution of the compound dissolved or suspended in an acceptable carrier, preferably an aqueous carder. A variety of aqueous carriers can be used, e.g., water, buffered water, 0.4% saline, and the like. These compositions will sometimes be sterilized by conventional, well known sterilization techniques, or can be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carders can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably less than about 20%.

EXAMPLES

The following examples are for the purpose of illustration only and are not intended to limit the scope of the invention in any manner.

EXAMPLE 1: Production of *Flavobacterium spp.* and Isolation of MRR-21

Bacteria from a stock culture were streaked onto a solid starch agar medium which was made of NZ Amine Type A (available from Sheffield, Norwich, N.Y.), Yeast Extract (Difco), Soluble Starch (Difco), Dextrose (Sigma, St. Louis, Mo.), Calcium Carbonate (Sigma) and Agar (Difco). The bacteria were incubated at 26° C. for one week under anaerobic conditions, after which a colony was selected from the plate for use as an inoculum to start a liquid broth culture of the bacterium. The broth culture was started in 250 ml of a broth comprising the same medium as just described in a 500 ml Erlenmeyer flask, but without agar. The culture was maintained at 26° C. for 24 hours.

About 1 ml of the broth culture was then added to 15 L of the medium in a 20 L dual vessel New Brunswick fermenter (Model MF-214/96325). The fermenter was aerated at a rate of 50 ml/min while agitating at 200 rpm for 96 hours. Following this, the cells were centrifuged (Sorval, Model RC-5 Superspeed Refrigerated Centrifuge) at about 3,000 rpm for about 15 minutes. This provided about 100 g of cells.

In a second culture method, the flavobacterium was also grown in 250 mL sterile Erlenmeyer flasks which included a seed medium containing 1.0% soy flour, 0.5% Bactopeptone, 0.5% beef extract, 0.05% di-basic potassium phosphate ($K_2HPO_4$), and 1% glucose at a pH of about 6.8. The bacteria were incubated at a temperature of about 28° C. for about 48 hours, whereupon an aliquot was transferred to a 20 L flask containing 1.0% dextrin, 1.3% soy flour, 0.6% Bactopeptone, 0.6% beef extract, 0.6% NaCl, 0.006% $K_2HPO_4$, 1.5% glucose and 0.1% Dow Coming Antifoam at a pH of about 7.0. A second aliquot (2%) was transferred to a 15 L New Brunswick fermenter and shaken at 250 rpm for 90–96 hours. The glucose concentration fell from 1.5% to 0.1–0.5% during this period. The pH fell to 5.0.

The cells were lysed with a 0.5% EDTA solution. The fats from the cells were then extracted with hexane. The extract was then extracted a second time with 2 L of ethyl acetate containing 1.0% chloroform (Aldrich, Milwaukee, Wis.). The washings were then concentrated to about 100 ml using a "Rotovap" (Wheaton, Model 413050) maintained at a temperature of about 30° C. The concentrate was then washed with 100 ml of a 1N sodium carbonate solution in a separatory funnel. An alternate isolation protocol comprises adjusting the pH of the broth to about 2.0 using 6N hydrochloric acid (HCl) and extracting the broth twice with ethyl acetate.

The aqueous fraction was discarded and about 100 ml of chilled water was added to the organic fraction and the mixture refrigerated overnight during which a precipitate formed. This precipitate was collected by filtration and dried to produce about 1–2 g of the desired product, MRR-21, a pale yellow crystal. Alternatively, the ethyl acetate extracts may be dried over sodium sulfate, filtered, and evaporated to dryness at a temperature of about 35° C. The residue is then washed once with ether and the washings are discarded. The remaining material may then be dissolved in chloroform/methanol/acetic acid (87:3:3). The product was then crystallized from this solution. In an alternate purification protocol, the ethyl acetate extracts were washed with about 5–10 ml of ethyl ether. The ether layer was reserved and the desired MRR-21 crystallized from the ether with ethyl acetate:methanol (50:50). The crystals were determined to have a melting point of about 188°–199° C., and the following elemental composition: carbon ca. 68.6%, hydrogen ca. 6.9%, oxygen ca. 24.4%. The UV spectrum of the crystals showed a maximum at about 223 nm in ethanol.

EXAMPLE 2: Antitumor Activity of MRR-21

A. Antitumor Activity Against Leukemia, Melanoma, and Colon and Renal Cancers

MRR-21 was subjected to the National Cancer Institute's primary antitumor screen. This screening comprises determining the activity of MRR-21 against sixty human cancer cell lines at a minimum of five concentrations at ten-fold dilutions. The sixty cell lines spanned nine forms of cancer, including leukemia, non-small cell lung cancer, CNS cancer, ovarian cancer, prostate cancer, breast cancer, colon cancer, renal cancer and melanoma. A standard 48-hour continuous drug exposure protocol was used and a sulfurhodamine B (SRB) protein assay was employed to determine the viability of cell growth. Factors which are observed during the screening program include mean response parameters, differential cellular sensitivity, and subpanel-specific patterns of sensitivity.

The results of the study indicated that MRR-21 was strongly effective against leukemia, and showed effectiveness against melanoma, and colon and renal cancers as illustrated in the dose response curves, FIGS. 1A–D respectively. FIG. 1A shows the dose-response curve for 5 leukemia cell lines exposed to MRR-21 as described above. The figure illustrates that MRR-21 performed uniformly with respect to all cell lines, showing a concentration effective to halt cell growth of between 0.56 mg/ml and 2.29 mg/ml. Table 2 below lists the concentrations of MRR-21 required to stop cell growth for each cell line tested.

TABLE 2

MRR-21 Activities Against Leukemia Cell Lines

| Cell Line | MRR-21 Concentration (mg/ml) |
| --- | --- |
| HL-60 | 0.56 |
| MOLT-4 | 0.85 |
| RPMI-8226 | 1.18 |

TABLE 2-continued

MRR-21 Activities Against Leukemia Cell Lines

| Cell Line | MRR-21 Concentration (mg/ml) |
| --- | --- |
| K-562 | 1.28 |
| CCRF-CEM | 2.29 |

Figure 1B:
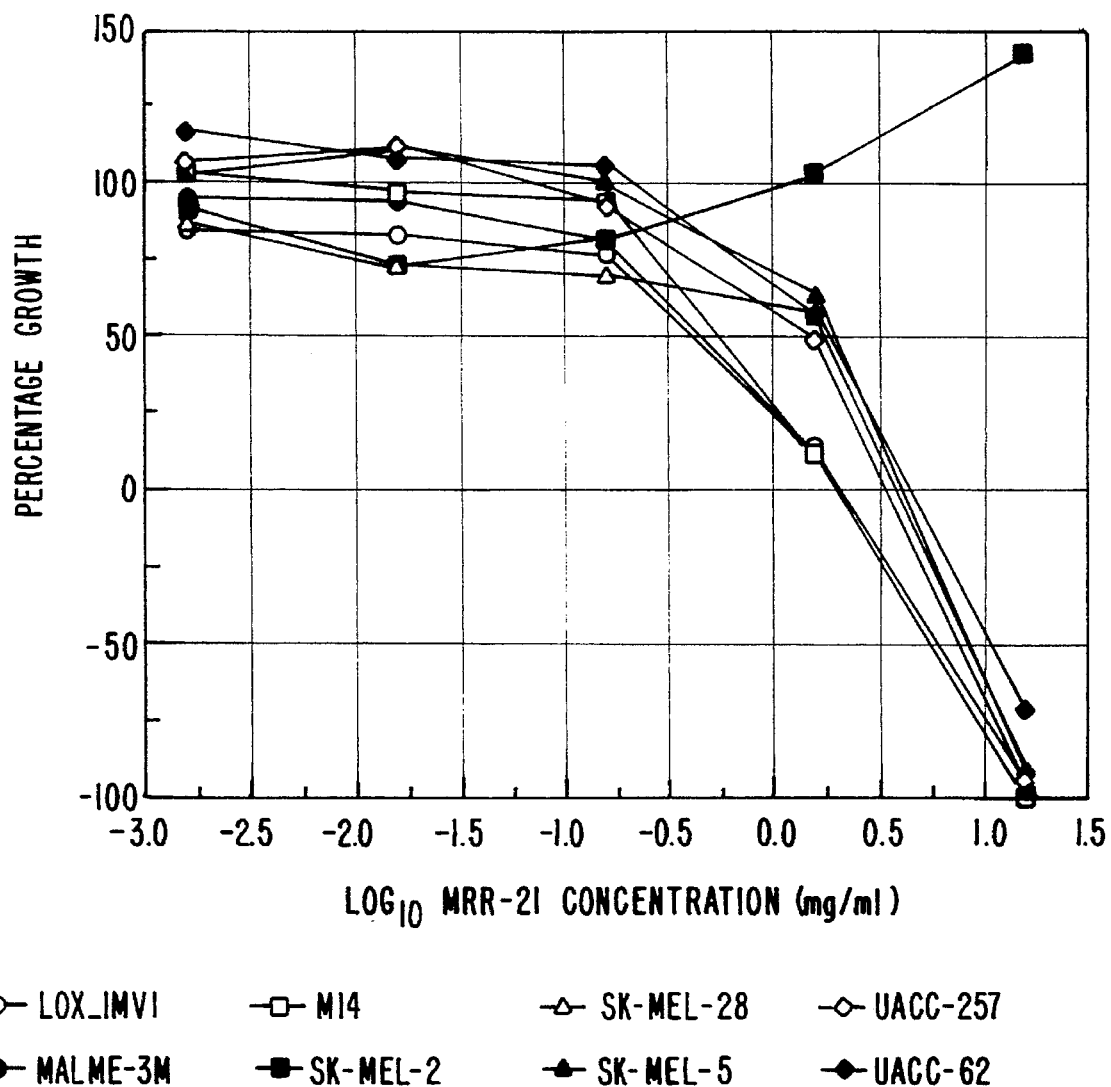

FIG. 1B illustrates the effectiveness of MRR-21 against 8 melanoma cell lines, showing uniform activity against all cell lines but one (SK-MEL-2), with concentration effective to stop cell growth between about 1.93 mg/ml and 4.05 mg/ml. Table 3 below lists the concentrations of MRR-21 required to stop cell growth for each cell line tested.

TABLE 3

MRR-21 Activities Against Melanoma Cell Lines

| Cell Line | MRR-21 Concentration (mg/ml) |
| --- | --- |
| MALME-3M | 1.93 |
| M14 | 1.93 |
| LOX-IMVI | 1.93 |
| UACC-257 | 3.43 |
| SK-MEL-28 | 3.73 |
| SK-MEL-5 | 3.73 |
| UACC-62 | 4.05 |
| SK-MEL-2 | NA |

Figure 1C:
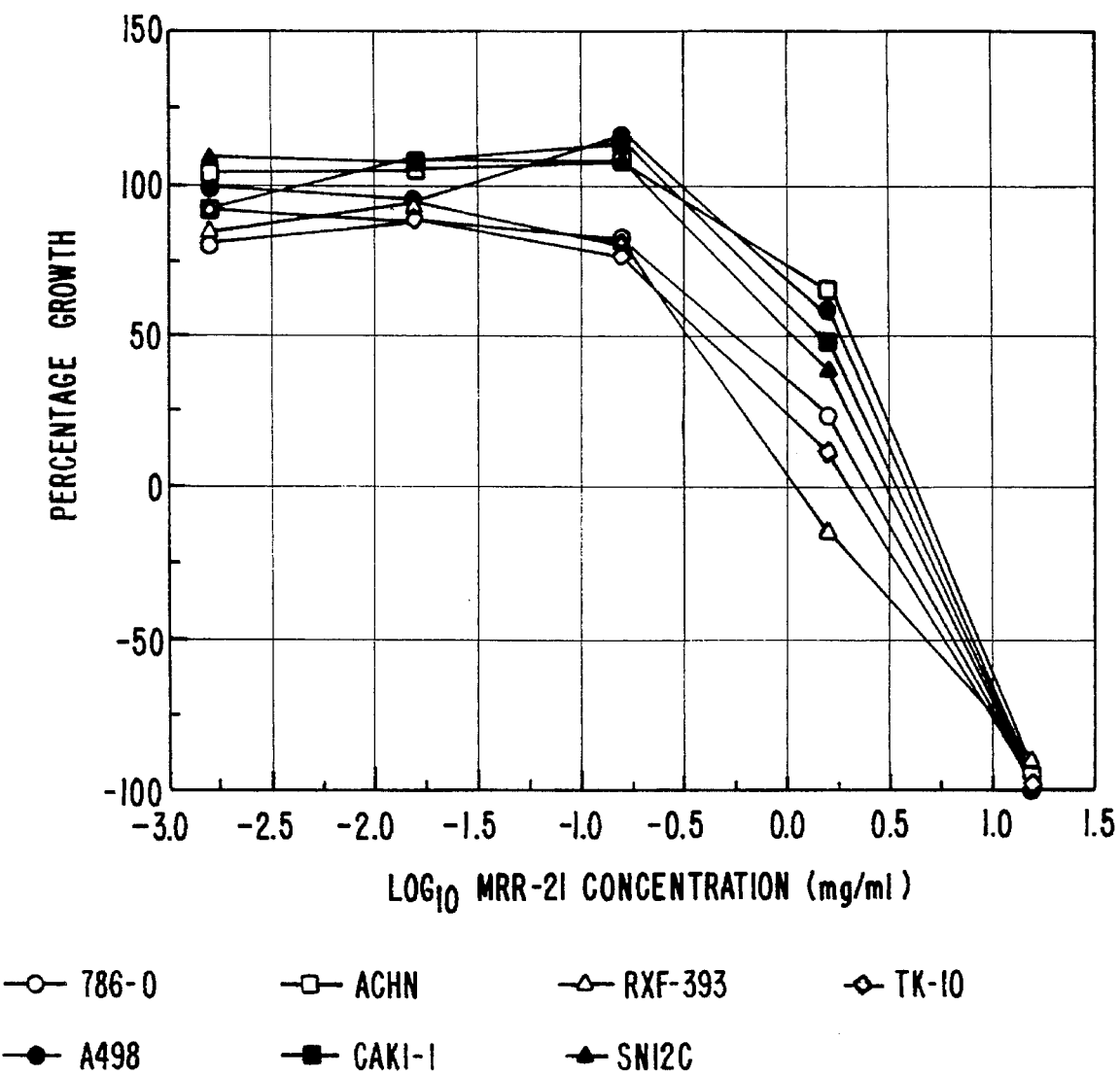

FIG. 1C demonstrates the activity of MRR-21 against renal cancer cell lines. Here too, the anti-tumor activity of MRR-21 is uniform with concentrations effective to completely inhibit cell growth of between about 1.93 mM and 4.05 mM. Table 4 illustrates the inhibitory concentration for MRR-21.

TABLE 4

MRR-21 Activities Against Renal Cancer Cell Lines

| Cell Line | MRR-21 Concentration (mg/ml) |
| --- | --- |
| RXF-393 | 2.29 |
| TK-10 | 1.93 |
| 786-0 | 2.37 |
| SN12C | 2.91 |
| CAKI-1 | 3.29 |
| ACHN | 4.05 |
| A498 | 3.73 |

Figure 1D:
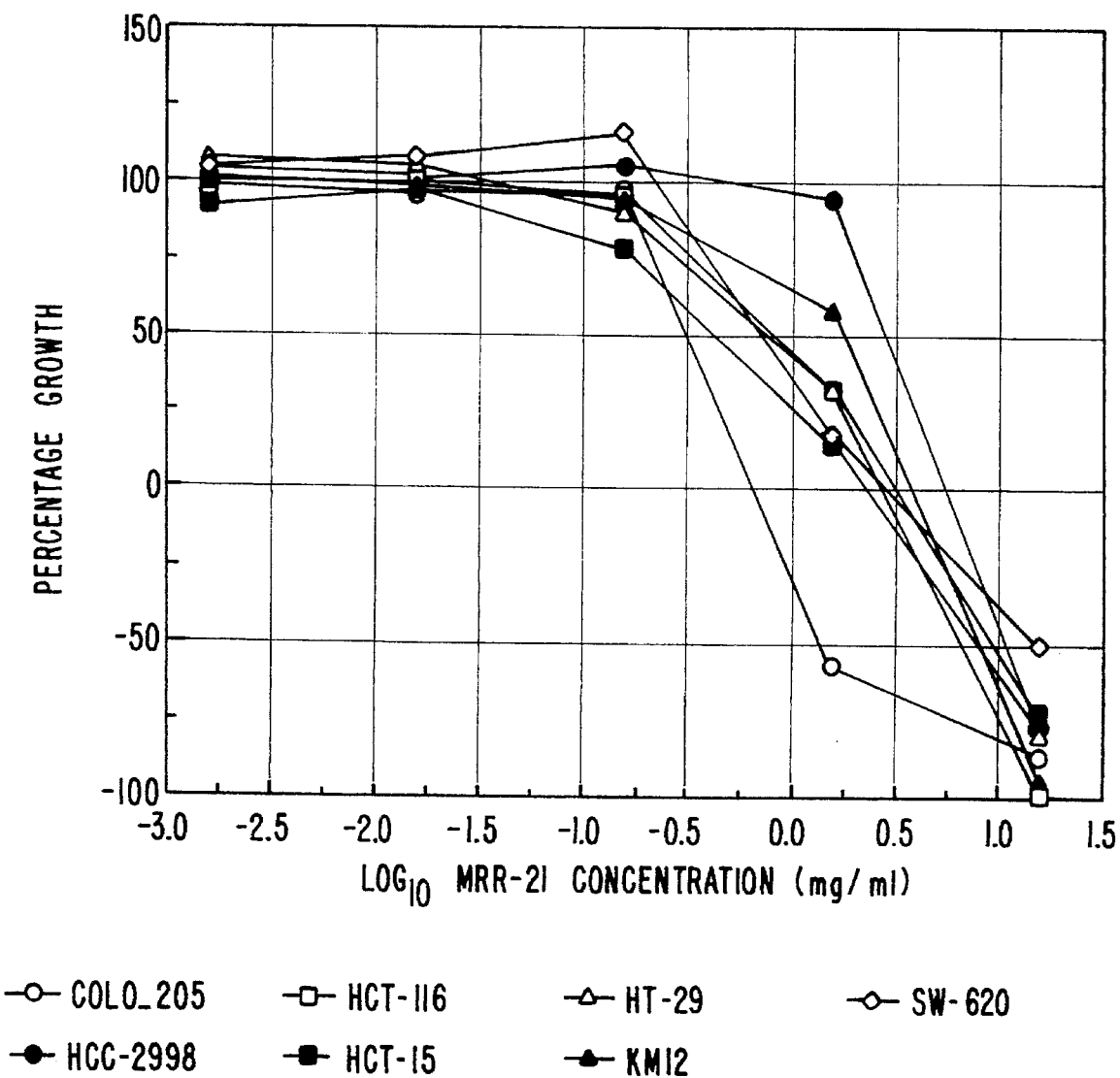

Finally, FIG. 1D shows the activity of MRR-21 against various colon cancer cell lines. Although there is some variation in activity, all cell lines responded to MRR-21, the most responsive being COLO 205. The concentrations of MRR-21 effective to halt cell growth ranged between 0.66 mM and 5.04 mM. The inhibitory concentrations for MRR-21 are shown in Table 5 below.

TABLE 5

MRR-21 Activities Against Colon Cancer Cell Lines

| Cell line | MRR-21 Concentration (mg/ml) |
| --- | --- |
| COLO-205 | 0.66 |

TABLE 5-continued

MRR-21 Activities Against Colon Cancer Cell Lines

| Cell line | MRR-21 Concentration (mg/ml) |
| --- | --- |
| HCT-15 | 2.18 |
| HCT-116 | 2.68 |
| SW-620 | 0.28 |
| HT-29 | 2.91 |
| KM12 | 3.73 |
| HCC-298 | 5.40 |

B. Studies On Mice Having Sarcoma-180 Tumors

Four groups of Swiss Webster mice (Tyler Laboratories), having an average weight of about 27 g, were used to test the effectiveness of MRR-21 in alleviating artificially induced Sarcoma-180 tumors. The groups of seven mice each were successfully transplanted with Sarcoma-180 (obtained from the Sloan-Kettering Institute, N.Y.) to a hind leg by intramuscular (IM) injection (0.1 ml of a suspension of about $1.0 \times 10^6$ Sarcoma-180 cells), and were treated with MRR-21 intraperitoneally (IP) per day for five days beginning 24 hr after transplantation. The mice were held for an additional five days following the last treatment day. The following results were observed:

TABLE 6

Weights (g) of individual disarticulated mouse legs 7 days after Introduction of Sarcoma-180 Cells
(7 Days of Observation And Treatment With MRR-21)

| Mouse | Group I Sarcoma-180 No MRR-21 | Group II No Sarcoma-180 No MRR-21 | Group III Sarcoma-180 MRR-21 (27 µg/kg) | Group IV Sarcoma-180 MRR-21 (270 µg/kg) |
| --- | --- | --- | --- | --- |
| 1 | 3.5 | 1.2 | 1.4 | 1.2 |
| 2 | 4.2 | 1.3 | 2.0 | 1.7 |
| 3 | 3.7 | 1.3 | 1.7 | 1.6 |
| 4 | 5.1 | 1.2 | 2.1 | 1.5 |
| 5 | 3.2 | 1.1 | 1.5 | 1.6 |
| 6 | 3.7 | 1.2 | 1.4 | 1.7 |
| 7 | 2.7 | 1.3 | 1.5 | 1.3 |
| Average Leg Weight (g) | 3.7 | 1.2 | 1.7 | 1.5 |

As the data indicate, mice with untreated tumors had hind-leg weights about 2.2 grams heavier on average as a result of unchecked tumor growth. Mice that received MRR-21 showed far smaller tumor mass on average.

The results of the treatment of the advanced-stage tumors are shown in Table 7. The tumors treated with MRR-21 showed a significant response to the drug. The hind legs of mice in Groups I, IIIa and IIIb were injected with Sarcoma-180 cells, and tumors were allowed to develop over a period of seven days. Over the following seven days, mice in Groups IIIa and IIIb received daily injections of MRR-21 at a dose of 100 µg/kg. Mice in Group I received no MRR-21 and mice in Group II received neither Sarcoma-180 nor MRR-21. On the fourteenth day following the Sarcoma-180 injections, the mice were sacrificed and their hind legs assayed.

TABLE 7

Weights (g) of Individual Disarticulated Mouse Hind Legs 14
Days After Introduction of Sarcoma-180 Cells
(7 Days Observation Followed By 7 Days of
Treatment With MRR-21)

| Mouse | Group I Sarcoma-180 No MRR-21 | Group II No Sarcoma-180 No MRR-21 | Group IIIa Sarcoma-180 MRR-21 @ (100 μg/kg) | Group IIIb Sarcoma-180 MRR-21 @ (100 μg/kg) |
|---|---|---|---|---|
| 1 | 3.5 | 1.5 | 2.5 | 1.9 |
| 2 | 3.1 | 1.5 | 2.1 | 3.1 |
| 3 | 3.3 | 1.6 | 2.3 | 2.3 |
| 4 | 4.2 | 1.4 | 3.1 | 1.8 |
| 5 | 2.9 | 1.5 | 2.9 | 3.0 |
| 6 | 3.2 | — | 1.9 | 2.2 |
| Average Leg Weight | 3.7 | 1.5 | 2.5 | 2.4 |
| Net Tumor Weight | 1.9 | 0.0 | 0.9 | 1.0 |

The data show the same dramatic reduction of tumor mass seen in the short-term study. This indicates that MRR-21 is effective against advanced tumors.

Table 8 shows the results of a longer term study. The same protocol as described above was followed, only the mice were sacrificed seven days following the completion of treatment. Again, MRR-21 was effective in reducing advanced tumor growth.

TABLE 8

Weights (g) of Individual Disarticulated Mouse Hind Legs 14 Days After
Introduction of Sarcoma-180 Cells
(7 Days Observation Followed By 7 Days of Treatment With MRR-21
Followed By An Additional 7 Days Of Observation)

| Mouse | Group I Sarcoma-180 No MRR-21 | Group II No Sarcoma-180 No MRR-21 | Group IIIa Sarcoma-180 MRR-21 (100 μg/kg) | Group IIIb Sarcoma-180 MRR-21 (100 μg/kg) | Group IIIc Sarcoma-180 MRR-21 (100 μg/kg) |
|---|---|---|---|---|---|
| 1 | 5.2 | 1.4 | 2.2 | 5.2 | 6.5 |
| 2 | 7.0 | 1.5 | 3.2 | 1.7 | 3.9 |
| 3 | 8.1 | 1.6 | 2.5 | 4.1 | 3.0 |
| 4 | 5.8 | 1.2 | 3.1 | 2.9 | 1.6 |
| 5 | 7.3 | 1.4 | 0.4 | 1.4 | 2.4 |
| 6 | 6.8 | — | 1.8 | 4.1 | 1.7 |
| Average Leg Weight | 6.7 | 1.4 | 2.5 | 3.2 | 3.2 |
| Net Tumor Weight | 5.3 | 0.0 | 1.1 | 1.8 | 1.8 |

C. The Effect Of MRR-21 On Leukemia P388 In Mice.

Ascites fluid from a passage mouse was implanted in C57 BL/6 mice. The inoculum was given IP. The mice were all males having body weights of about 18–21 grams. The inoculum was 0.1 ml of diluted ascites fluid containing $1 \times 10^6$ P388 cells. Treatment was done in a single dose of a saline solution containing MRR-21 IP on day 1 at 20 mg/kg body wt of each of the test materials. The parameter used for measuring efficacy is median survival time.

All survivors were sacrificed 30 days following exposure to P388 and examined for evidence of ascites. The results are shown in Table 9 below (a "*" indicates a statistically significant result).

TABLE 9

| | Effect of MRR-21 on P-388 | | | |
|---|---|---|---|---|
| Extract | No. of Mice | No. Survivors at 14 Days | No. Survivors at 21 Days | No. Survivors at 30 Days |
| Saline | 20 | 0 | — | — |
| MRR-21 @ 10.0 mg/kg | 20 | 20 | 15 | 12* |
| MRR-21 @ 20.0 mg/kg | 20 | 20 | 20 | 20* |

EXAMPLE 3: ANTI-INFLAMMATORY ACTIVITY OF MRR-21

MRR-21 also exhibits anti-inflammatory properties as illustrated below. The testing method described by Robert, A. and Nezamis, J. E., "The granuloma pouch as a routine assay for antiphlogistic compounds," *Acta Endocrinologica* 25, 105–112, (1957) was employed. One hundred Sprague-Dawley male white rats weighing 200–250 grams each were divided into four test groups with ten rats in each group. The rats were confined to individual cages at a temperature of about at 70° F. The rats had free access to food and fresh water at all times. All test materials were administered intraperitoneally. Treatment was carded out five consecutive days starting the day following pouch preparation. The results are shown in Table 10 below.

TABLE 10

Summary of Treatment, Body Weight Gains and
Volume of Granuloma Pouch Exudate

| Group | Treatment | No. Rats | Average Weight Gain (g) | Average Pouch Exudate (ml) | % Inhibition |
|---|---|---|---|---|---|
| I | 0.5 ml saline | 10 | 14.6 | 7.2 | — |
| II | Hydrocortisone 10 mg/kg body wt. | 10 | 4.6 | 3.7 | 49 |
| III | MRR-21, 5 mg/kg body wt. | 10 | 14.2 | 3.9 | 46 |
| IV | MRR-21 10 mg/kg | 10 | 13.5 | 1.1 | 85 |

The results indicate that MRR-21 has an anti-inflammatory activity greater than hydrocortisone.

Thus, advantages of the invention will now be apparent. The invention can be seen to provide a source of substantially pure bacterium which produces a composition which has remarkable anti-tumor and anti-inflammatory effects. While the invention has been particularly shown and described with reference to preferred embodiments thereof, it will be understood by those skilled in the an that the foregoing and other changes in the form and details may be made therein without departing from the spirit or scope of the invention.

All references disclosed herein, both patent and non-patent, are expressly incorporated by reference for all purposes.

What is claimed is:

1. A biologically pure culture of *Flavobacterium sp.* ATCC 55435.

2. A biologically pure culture having all of the identifying characteristics of the *Flavobacterium sp.* ATCC 55435.

* * * * *